(12) United States Patent
Stuke et al.

(10) Patent No.: US 8,472,018 B2
(45) Date of Patent: Jun. 25, 2013

(54) GRATING FOR MULTIPLE DISCRETE WAVELENGTHS OF RAMAN SCATTERING

(75) Inventors: Michael J. Stuke, Palo Alto, CA (US); Michael R. T. Tan, Menlo Park, CA (US); Alexandre M. Bratkovski, Mountain View, CA (US); Min Hu, Sunnyvale, CA (US); Huei Pei Kuo, Cupertino, CA (US); Jingjing Li, Palo Alto, CA (US); Zhiyong Li, Redwood City, CA (US); Fung Suong Ou, Palo Alto, CA (US); Shih-Yuan Wang, Palo Alto, CA (US); Wei Wu, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 341 days.

(21) Appl. No.: 12/847,982

(22) Filed: Jul. 30, 2010

(65) Prior Publication Data

US 2012/0026493 A1    Feb. 2, 2012

(51) Int. Cl.
*G01J 3/44*    (2006.01)

(52) U.S. Cl.
USPC ...................................................... 356/301

(58) Field of Classification Search
USPC ............................................ 356/72–73, 301
See application file for complete search history.

(56) References Cited

U.S. PATENT DOCUMENTS

| | | | |
|---|---|---|---|
| 6,657,723 B2 | 12/2003 | Cohen et al. | |
| 7,151,599 B2 | 12/2006 | Islam et al. | |
| 7,397,559 B1 | 7/2008 | Bratkovski | |
| 2009/0147254 A1 | 6/2009 | Kirby | |
| 2010/0085566 A1* | 4/2010 | Cunningham | 356/301 |

OTHER PUBLICATIONS

Kahl, M. et al., "Optimization of Periodic Structures for Surface Enhanced Raman Scattering", Progress in Surface Raman Spectroscopy, Theory, Techniques and Applications, IC ORS 2000 meeging, Xiamen. China (Aug. 14-17, 2000) pp. 1-2.

Kahl, M. et al., "Periodically Structured Metallic Substrales for SERS" Sensors and Actuators B: Chemical, vol. 51, Issues 1-3, (Aug. 31, 1998) pp. 285-291.

Liu, D. et al., "Improvement of the wavelength selectivity of volume holographic gratings for optical communication," Journal of Optics A: Pure and Applied Optics 11 (2009) 065404 (pp. 1-6).

* cited by examiner

*Primary Examiner* — Tarifur Chowdhury
*Assistant Examiner* — Abdullahi Nur

(57) ABSTRACT

Systems and methods employ a layer having a pattern that provides multiple discrete guided mode resonances for respective couplings of separated wavelengths into the layer. Further, a structure including features shaped to enhance Raman scattering to produce light of the resonant wavelengths can be employed with the patterned layer.

19 Claims, 2 Drawing Sheets

GRATING FOR MULTIPLE DISCRETE WAVELENGTHS OF RAMAN SCATTERING

BACKGROUND

Raman scattering generally refers to the inelastic scattering of photons. When light scatters from an atom or molecule, a fraction of the photons induces a transition to or from an excited state of the atom or molecule, which produces scattered photons having a different frequency from the frequency of incident photons. The frequencies of the Raman scattered photons are characteristic of the atoms or molecules from which the photons scatter, which permits spectral analysis to identify chemical analytes. However, the fraction of photons scattered by Raman scattering is generally small, e.g., about 1 per $10^7$ elastically scattered photons, and methods for enhancing the signal associated with Raman scattering have been developed. In particular, Surface Enhanced Raman Scattering (SERS) enhances the Raman scattering through interactions of scattered photons with rough metal surfaces or nanoparticles. Such enhancement is believed to result from resonances in localized surface plasmons interacting with photons and analytes. Methods and systems for further enhancing the Raman scattering signal and/or improving chemical analysis based on Raman scattering are sought.

BRIEF DESCRIPTION OF THE DRAWINGS

Use of the same reference symbols in different figures indicates similar or identical items.

DETAILED DESCRIPTION

In accordance with an aspect of the invention, a SERS system can employ a guided mode resonance (GMR) grating with a pattern that is optimized for multiple separated wavelengths. In particular, instead of having a constant period or a chirped period, the grating has parameters that vary as necessary to provide resonant couplings for a set of discrete wavelengths. The resonant wavelengths can all be different wavelengths associated with the same analyte, e.g., the same molecule or atom, for use in a system having enhanced selectivity in the detection of a single analyte. Alternatively, the wavelengths can be associated with different analytes for a system capable of detecting a number of different analytes. The pattern required to achieve the desired performance can be determined through a suitable transform such as a Fourier transform of the desired coupling strengths to produce a grating pattern that achieves the desired coupling strengths.

Figure 1:
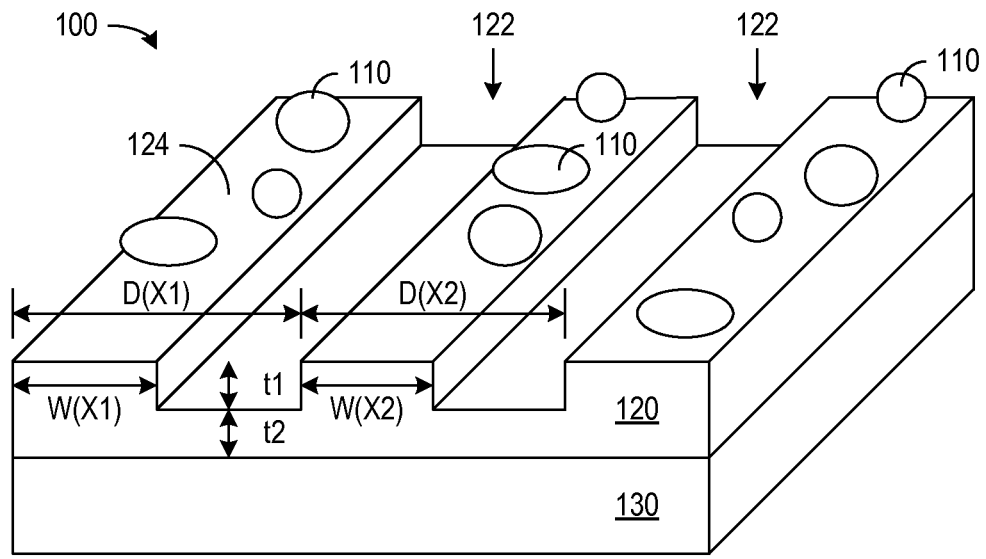
FIG. 1 illustrates a system in accordance with an embodiment of the invention using a line grating having parameters that vary to produce resonances at multiple light frequencies.

FIG. 1 illustrates a grating system 100 in accordance with an embodiment of the invention based on a line grating pattern. In some embodiments, system 100 may be employed in a spectroscopy apparatus used for detection of one or more specific analytes in a sample or the surrounding environment system 100. System 100 could also be used in a sensor system adapted to detect one particular analyte or any analyte from a targeted set of analytes. In particular, system 100 includes a SERS layer 110 that would generally be positioned to come into contact or close proximity to atoms or molecules of one or more analytes. SERS layer 110 may, for example, be the top layer of system 100 and may be exposed to the air of the surrounding environment. Alternatively, SERS layer 110 may be in a channel through which a gaseous or liquid sample flows or resides. SERS layer 110 generally includes features that interact electromagnetically with photons or analytes to enhance Raman scattering of photons from the analytes. As mentioned above, such enhancement is believed to result from interactions with resonances of surface plasmons in conductive features of SERS layer 110. SERS layer 110 in the illustrated embodiment includes particles, e.g., gold or silver particles having sizes on the order of several or tens of nanometers. In the illustrated embodiment, particles in SERS layer 110 can be fabricated and then applied system 100 so that the particles will be at least partly in an evanescent field of guided mode resonances of a GMR layer 120. Alternatively, SERS layer 110 can be fabricated on or overlying GMR layer 120 to position SERS features in the evanescent field of guided mode resonances.

GMR layer 120 includes a grating pattern that varies across the area of system 100 as required to provide guided mode resonances for a discrete set of wavelengths within GMR layer 120. Guided mode resonances, which are sometimes referred to as "leaky resonances," are understood in the art to correspond to resonances excited in a waveguide by a phase-matching element such as a diffraction grating. In general, a signal (e.g., light) incident on GMR layer 120 will be strongly coupled into a resonance mode in GMR layer 120 only under specific circumstances, e.g., when specific conditions on the direction, the wavelength, and possibly the polarization of the incident light are satisfied. In a system where the incident direction of the light signal is fixed, the condition for guided mode resonance in GMR layer 120 is that the incident light has one of the discrete wavelengths $\lambda_1$ to $\lambda_N$ for an integer N equal to or greater than 2, e.g., $2 \leq N \leq 5$ or more.

FIG. 1 illustrates an embodiment of GMR layer 120 in which a grating pattern and a waveguide are made of the same material, e.g., a layer of a dielectric material such as silicon nitride. Alternatively, GMR layer 120 can include layers of different materials, for example, a layer in which a grating pattern is formed and a layer that acts as a waveguide. Also, the grating pattern in GMR layer 120 can be formed using regions of solid materials having different refractive index, instead of using air gaps formed in a solid layer as shown in FIG. 1.

The grating pattern of FIG. 1 particularly includes a series of grooves 122 of depth t1, which leaves a thickness t2 of GMR layer 120 beneath grooves 122. In general, thickness t2 can be 0, so that grooves 122 pass through GMR layer 120. Grooves 122 leave stripes 124 of thickness t1+t2 and width W, and the combined widths of a stripe 124 and a groove 122 is referred to herein as the period D of the grating pattern. The ratio W/D of the width W of a stripe to the period D defines the duty cycle of the period containing the stripe. The period D and width W of stripes 124 in GMR layer 120 can be smaller than the wavelength of the signal light. In accordance with an aspect of the invention, parameters, particularly the period D, the width W, or the duty cycle W/D of the grating pattern of GMR layer 120 varies across the area of system 100 in a manner that provides guided mode resonances in GMR layer 120 for a target incidence angle and the desired wavelengths $\lambda_1$ to $\lambda_N$. Further, the coupling into the guided mode resonances can be provided across the entire area of the grating pattern, instead of in a patchwork fashion where different separate areas of the grating pattern each couple incident signal light into a corresponding only one of the guided modes.

The grating pattern of FIG. 1 being based on grooves 122 may provide couplings to the guide mode resonances that are dependent on the polarization of incident light. In particular, light having a linear polarization parallel or perpendicular to grooves 122 may experience different couplings into waveguide layer 120. In many applications, the polarization difference is not critical, for example, when the polarization of incident light is fixed and anticipated in the design of the grating pattern. However, a two-dimensional grating may be employed to reduce or eliminate polarization dependence.

Figure 2:
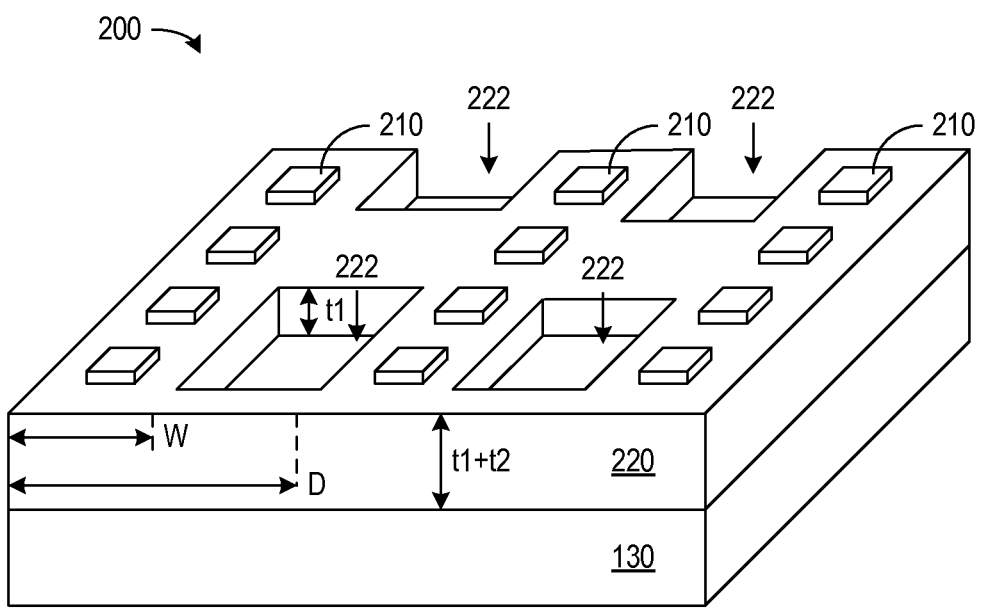
FIG. 2 illustrates a system in accordance with an embodiment of the invention using a two-dimensional grating pattern with parameters that vary to produce resonances at separated frequencies of light.

FIG. 2 shows an embodiment of a grating system 200 in which a GMR layer 220 has a two-dimensional grating pattern. In the illustrated embodiment, the grating pattern is formed using air gap regions 222 in GMR layer 220, but a two-dimensional grating pattern could alternatively be formed using regions of solid material having different refractive indexes. Regions 222, which are square or rectangular in FIG. 2, could alternatively have any desired shape. Also, the grating pattern in GMR layer 220 could be formed in a layer of material that is different from the material used as a waveguide within GMR layer 220. The two-dimensional grating pattern of FIG. 2 could have periods and duty cycles along one direction that are the same as or that differ from the periods and duty cycles along a perpendicular direction. In accordance with an aspect of the current invention, the period and duty cycle of the grating pattern of GMR layer 220 varies across the area of GMR layer 220 in order to provide guided mode resonances for a set of discrete wavelengths $\lambda_1$ to $\lambda_N$.

System 200 as shown in FIG. 2 also illustrates an SERS layer 210 that is made of discrete metal regions formed on or overlying GMR layer 220. Such regions may enhance Raman scattering from nearby analyte atoms or molecules through plasmon interactions. Raman scattering can be further enhanced through interactions with the evanescent field that results outside of GMR layer 220 when GMR layer 220 contains light in a guided mode resonance.

FIGS. 1 and 2 illustrate embodiments of the invention in which GMR layers 120 and 220 are fabricated on a carrier substrate 130. Carrier substrate 130 may have a refractive index less than that of GMR layer 120 or 220 for total internal reflections of light in the guided modes of GMR layer 120 or 220. For example, substrate 130 could be a glass substrate when GMR layer 120 or 220 employs a silicon nitride waveguide. More generally, the materials selected for GMR layer 120 or 220 and carrier substrate 130 can be selected according to the wavelengths of light being guided. Alternatively, the carrier substrate could be eliminated to provide a freestanding GMR layer 120 or 220. More generally, systems 100 and 200 may be integrated onto or into essentially any surface using many conventional manufacturing methodologies including, but not limited to microlithography-based surface patterning and nanolithography-based surface patterning such as used in integrated circuit fabrication. For example, conventional semiconductor manufacturing techniques (e.g., a CMOS compatible fabrication process) may be employed to create a GMR grating on or in a surface of a photonic integrated circuit (IC). In which case, system 100 or 200 may be readily integrated with conventional photonic or electronic systems on a monolithic chip. Moreover, such an exemplary IC-based system may have a surface footprint as small as one square millimeter (mm) or less when fabricated using currently available manufacturing methods.

Figure 3:
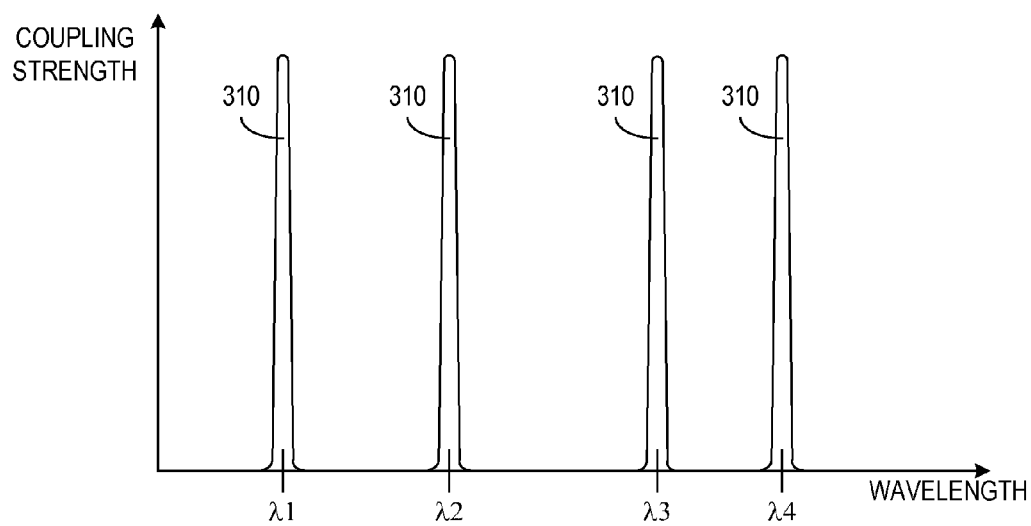
FIG. 3 is a graph of a desired coupling strength as a function of the wavelength of the light coupled into waveguide layer.

The grating patterns and parameters of GMR layers as described above create guided mode resonances for multiple wavelengths $\lambda_1$ to $\lambda_N$ that are incident at a target angle. FIG. 3 illustrates the functional dependence of the coupling strength of a GMR layer in accordance with an exemplary embodiment of the invention. In particular, the coupling strength shown in FIG. 3 has resonance peaks 310 associated with wavelengths $\lambda_1$, $\lambda_2$, $\lambda_3$, and $\lambda_4$. Resonance peaks 310 have widths for acceptance of light wavelengths into the resonant mode, and such widths depend on the quality or Q factor of the resonance. FIG. 3 shows resonance peaks 310 that have the same quality and strength. More generally, the resonant couplings for different wavelengths may differ in strength and quality. For example, the properties of resonance peaks 310 for different wavelengths may be selected to provide specific relative Raman scattering signal strengths for different wavelengths $\lambda_1$, $\lambda_2$, $\lambda_3$, and $\lambda_4$. In accordance with an aspect of the invention, a grating pattern for a GMR layer can be selected to correspond to a transform of a desired coupling strength function having multiple separated peaks. In particular, the resonance frequencies determine the required and most useful grating dimensions and periodic surface structure or structures.

Figure 4:
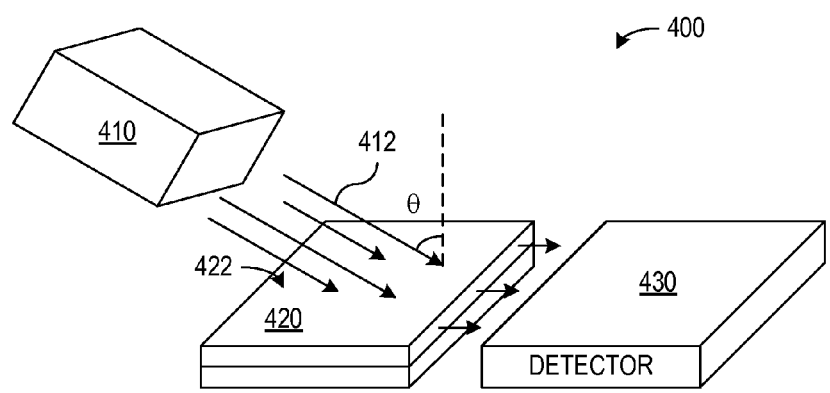
FIG. 4 illustrates use of a grating system such as illustrated in FIGS. 1 and 2 in a chemical analysis system.

FIG. 4 shows a scattering spectroscopy, chemical analysis, or sensor system 400 in accordance with an embodiment of the invention. As illustrated, system 400 includes a light source 410 such as a laser, a SERS/grating system 420 such as grating system 100 of FIG. 1 or grating system 200 of FIG. 2, and a detector 430. In operation of system 400, light source 410 produces an excitation signal 412 that illuminates system 420 at a fixed or variable incidence angle. Excitation signal 412 has an angle of incidence θ between 0° and 90°, and the angle of incidence is generally selected according to the target angle at which the grating structure is designed to produce the desired guided mode resonances. Excitation signal 412 may contain polarized light, for example, having a transverse electric (TE) polarization or transverse magnetic (TM) polarization. In some embodiments, excitation signal 412 is a monochromatic collimated light beam having a wavelength selected so that Raman scattering from a specific analyte or specific set of analytes produces scattered light with wavelengths $\lambda_1$ to $\lambda_N$.

System 420 is exposed to an analyte 422 while being illuminated by light source 410, so that excitation signal 412 interacts with analyte 422 to produce a scattered signal corresponding to Raman scattered photons. The scattered signal may be enhanced by an SERS layer in system 420. System 420 also includes a GMR layer, and the guided mode resonances established in the GMR layer produce an evanescent electromagnetic field that can interact with the Raman scattering process. The evanescent field interactions thus can further enhance the scattering signal for those specific wavelengths $\lambda_1$ to $\lambda_N$ that correspond to the guided mode resonances.

Light coupled into the GMR layer of system 420 is directed to a detector 430. Detector 430 may include, for example, a photodiode or other broadband light detector capable of measuring the intensity of light in a wavelength range including resonance wavelengths $\lambda_1$ to $\lambda_N$. Alternatively, detector 430 may include narrow band detectors capable of distinguishing between wavelengths $\lambda_1$ to $\lambda_N$. Such narrow band detectors could employ appropriate filters that select the resonance wavelengths $\lambda_1$ to $\lambda_N$. Alternatively, a dispersive element, which separates the different wavelengths spatially, could be used, so that resonance wavelengths $\lambda_1$ to $\lambda_N$ can be detected simultaneously by a position-sensitive detector, such as a tandem multichannel plate detector. Although detector 340 is shown as a separate component in FIG. 4, detector 430 and system 420 can alternatively be integrated into the same monolithic chip to provide a compact chemical sensor.

In some embodiments of system 400, SERS/grating system 420 is implemented to have guided mode resonances corresponding to different Raman scattering wavelengths $\lambda_1$ to $\lambda_N$ that correspond to Raman scattering of excitation signal 412 from one specific or targeted analyte. The detection of multiple Raman scattered wavelengths can improve selectivity for the targeted analyte. Further, enhancement of the Raman scattering frequencies of the targeted analyte by interactions with the guided mode resonances of system 420 can further improve selectivity of detection of the targeted analyte.

In some other embodiments of system 400, SERS/grating system 420 is implemented to have guided mode resonances corresponding to wavelengths $\lambda_1$ to $\lambda_N$ that respectively correspond to Raman scattering of excitation signal 412 from N targeted analytes. System 400 can thus detect any analyte from a set of targeted analytes. For example, in embodiment where detector 430 is a broadband detector, a warning signal may be generated when any of the target analytes are detected, e.g., when any analyte from a set of toxic or explosive compounds is detected. In an embodiment where detector 430 can distinguish among wavelengths $\lambda_1$ to $\lambda_N$, the specific analytes from the targeted set can be detected or identified.

Although the invention has been described with reference to particular embodiments, the description is only an example of the invention's application and should not be taken as a limitation. For example, although some of the above embodiments are described as employing light or optical signals, those terms include electromagnetic radiation generally and are not intended to be limited to visible light. Various other adaptations and combinations of features of the embodiments disclosed are within the scope of the invention as defined by the following claims.

What is claimed is:

1. A system comprising: a layer; a grating pattern that provides a plurality of discrete guided mode resonances for respective couplings of a plurality of separated wavelengths into the layer, wherein the separated wavelengths correspond to specific wavelengths of light Raman scattered from one or more targeted analytes; and a structure that is adjacent to the layer and includes features shaped to enhance Raman scattering that produces light of the specific wavelengths.

2. The system of claim 1, wherein the grating pattern corresponds to a transform of a coupling distribution having peaks at the separated wavelengths.

3. The system of claim 1, wherein the grating pattern is such that of each of the separated wavelengths is coupled into the layer from an entire area of the grating pattern.

4. The system of claim 1, wherein the system comprises a monolithic chip including the layer and the structure.

5. The system of claim 1, wherein each of the separated wavelengths corresponds to a wavelength of light that results from Raman scattering from a different analyte.

6. The system of claim 1, wherein each of the separate wavelengths corresponds to a different wavelength of light that results from Raman scattering from an analyte.

7. The system of claim 1, further comprising:
a light source positioned to illuminate the structures; and
a detector position to receive light coupled into the first layer.

8. The system of claim 1, wherein the detector comprises a system selected from a group consisting of:
a detector having a detection band that includes the wavelengths;
a plurality of detectors having detection bands respectively corresponding to the wavelengths; and
a dispersive element that separates the wavelengths spatially and a position sensitive detector positioned to separately measure the wavelength separated by the dispersive element.

9. The system of claim 1, wherein the features are at least partially positioned to be within an evanescent field of the guided mode resonances.

10. The system of claim 1, wherein the grating pattern is in the layer.

11. The system of claim 1, wherein the grating pattern has a period that varies in a manner that provides guided mode resonances in the layer for a target incidence angle and the separated wavelengths.

12. A method comprising: exposing a system to a sample, wherein the system includes: a grating pattern that provides a plurality of discrete guided mode resonances for respective couplings of a plurality of separated wavelengths into a layer, wherein the separated wavelengths correspond to specific wavelengths of light Raman scattered from one or more targeted analytes; and a structure that is adjacent to the layer and exposed to the sample, wherein the structure includes features shaped to enhance Raman scattering that produces light of the specific wavelengths; illuminating the system with an excitation beam; and measuring light in the guided mode resonances to detect any of the one or more targeted analytes.

13. The method of claim 12, wherein the grating pattern is such that each of the separated wavelengths is coupled into the layer from an entire area of the grating pattern.

14. The method of claim 12, wherein each of the separate wavelengths corresponds to a different wavelength of light that results from Raman scattering from an analyte.

15. The method of claim 12, wherein each of the separated wavelengths corresponds to a wavelength of light that results from Raman scattering from a different analyte from among the targeted analytes.

16. The method of claim 15, further comprising generating in response to measuring light a signal indicating that one of the targeted analytes was detected.

17. The method of claim 15, further comprising separately measuring the wavelengths to identify which of the targeted analytes are in the sample.

18. The method of claim 12, wherein the grating pattern is a transform of desired coupling strengths of the separated wavelengths into the layer.

19. The method of claim 12, wherein the grating pattern is in the layer.

* * * * *